United States Patent [19]

Lee

[11] Patent Number: 5,210,588
[45] Date of Patent: May 11, 1993

[54] FINGERPRINT IDENTIFICATION APPARATUS FOR ENHANCING IDENTIFICATION PERFORMANCE BY FORMING AN ILLUMINATION SOURCE AND A LIGHT CONDUCTING PANEL IN A SINGLE BODY

[75] Inventor: Ho-Gyu Lee, Seoul, Rep. of Korea

[73] Assignee: Goldstar Co., Ltd., Seoul, Rep. of Korea

[21] Appl. No.: 792,700

[22] Filed: Nov. 15, 1991

[30] Foreign Application Priority Data

Nov. 17, 1990 [KR] Rep. of Korea ............ 90-17681[U]

[51] Int. Cl.$^5$ .............................................. G06K 9/28
[52] U.S. Cl. ..................................... 356/71; 382/4
[58] Field of Search ............................. 356/71; 382/4

[56] References Cited

U.S. PATENT DOCUMENTS

| | | | |
|---|---|---|---|
| 4,120,585 | 10/1978 | De Palma et al. | 356/71 |
| 4,924,085 | 5/1990 | Kato et al. | 356/71 X |
| 5,077,803 | 12/1991 | Kato et al. | 356/71 X |

FOREIGN PATENT DOCUMENTS 61-48707 3/1986 Japan ..................................... 356/71

Primary Examiner—Vincent P. McGraw

[57] ABSTRACT

A fingerprint identification apparatus includes an illuminating member, a light conducting panel and a light concentration lens formed into a single body for easily assembling and preventing noise produced by the light conducting panel. Also, an ultra-luminance chip coated with a diffuser compound, and a rheostat installed to identify a fingerprint image formed by an imaging lens accurately and clearly enhances the reliability of the fingerprint identification apparatus.

5 Claims, 3 Drawing Sheets

FINGERPRINT IDENTIFICATION APPARATUS PERFORMANCE BY FORMING AN ILLUMINATION SOURCE AND A LIGHT CONDUCTING PANEL IN A SINGLE BODY

BACKGROUND OF THE INVENTION

This invention relates to a fingerprint identification apparatus and more particularly, to an apparatus for enhancing the identification performance by reducing noises produced during the process of fingerprint identification, and facilitating the process of manufacturing and assembly.

In general, there are two ways to identify a fingerprint, i.e., identifying a fingerprint by imaging only light totally reflected from the valley areas of a fingerprint, and by imaging only light diffused from the ridge areas of a fingerprint.

As shown in FIG. 1, a conventional and widely used fingerprint identification apparatus includes a rectangular prism 3 on which a fingerprint is placed for identifying the fingerprint, a multiple LED 2 for radiating light to the fingerprint, an imaging lens 4 for forming images in response to the light totally reflected from the valley areas of the fingerprint, a CCD (Charge Coupled Device) 5 for converting the image to an electrical signal after the image has been formed by the imaging lens 4, a signal processing circuit 6 for analyzing and processing the electrical signal received from the CCD 5, and a select switch 7 for activating the signal processing curcuit 6.

This type of conventional fingerprint identification apparatus is operated by first putting the fingerprint on the oblique plane of the rectangular prism 3. The select switch 7 is then pushed "ON", and the light radiated from the multiple LED 2 is reflected on the valley areas of the fingerprint. Therefore, an image is formed by the imaging lens 4, the image is converted to an electrical signal by the CCD 5 and transmitted to the signal processing circuit 6, and the signal processing circuit 6 identifies the fingerprint.

However, in the conventional fingerprint identification apparatus, the space between each of the LED chips 8 of the multiple LED 2 causes generally inconsistent intensity of radiation as shown in FIG. 3. Thus, it is difficult to obtain a clear image. In order to compensate for this problem, the conventional apparatus must be assembled to maintain a regular distance d from the rectangular prism 3, as illustrated in FIG. 1.

In addition, as shown in FIG. 2, when the fingerprint is placed on the rectangular prism 3 made from a solid material such as glass, a noise is produced because total reflection results from microgaps existing in the ridge areas r of the fingerprint, and the noise causes difficulties in identifying the image of the ridge and the valley areas of the fingerprint. To prevent these noises, generally, the surface of the commonly used rectangular prism 3 is coated with an elastic layer 9 of silicone of a regular thickness.

Also, the conventional apparatus described above has the following deficiencies.

Whenever an identification of the fingerprint is required, the select switch 7 must be operated for activating the signal processing circuit 6 in order to obtain the image of the fingerprint in every case. In addition, the assembling of the apparatus is difficult because the regular space must be maintained between the rectangular prism 3 and the multiple LED 2 to compensate for the inconsistent intensity of radiation according to the characteristics of the multiple LED 2. In cases where foreign substances such as dust exists between the rectangular prism 3 and the multiple LED 2, it is difficult to identify the fingerprint image because of the noises caused by the foreign substances.

Also, the fingerprint image formed by the imaging lens 4 and the CCD 5 may be distorted due to noises caused by bubbles existing within the silicone layer 9, coated on the rectangular prism 3 in order to prevent total reflection from the ridge areas of the fingerprint.

SUMMARY OF THE INVENTION

This invention is intended to solve the aforementioned problems. This invention facilitates the assembly of the apparatus by forming a light conducting panel and an illumination source into one body, and prevents noises produced due to the existance of foreign substances such as, etc. Further, the present invention uses a separate light concentration lens and sensing means, which makes it possible to identify a fingerprint automatically without having to operate a separate switch to obtain an image when the fingerprint is placed on the light conducting panel.

An object of invention is to facilitate assembly by making the light conducting panel and the illumination source into one body, and to provide a fingerprint identification apparatus capable of identifying a fingerprint accurately through the elimination of noises caused by the presence of foreign substances such as between the light conducting panel and the illumination source.

Another object of the invention is to provide a fingerprint identification apparatus which, by using the sensing means separate from the light concentration lens, can automatically identify the fingerprint without the need to operate a separate switch when the fingerprint is placed on the light conducting panel.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
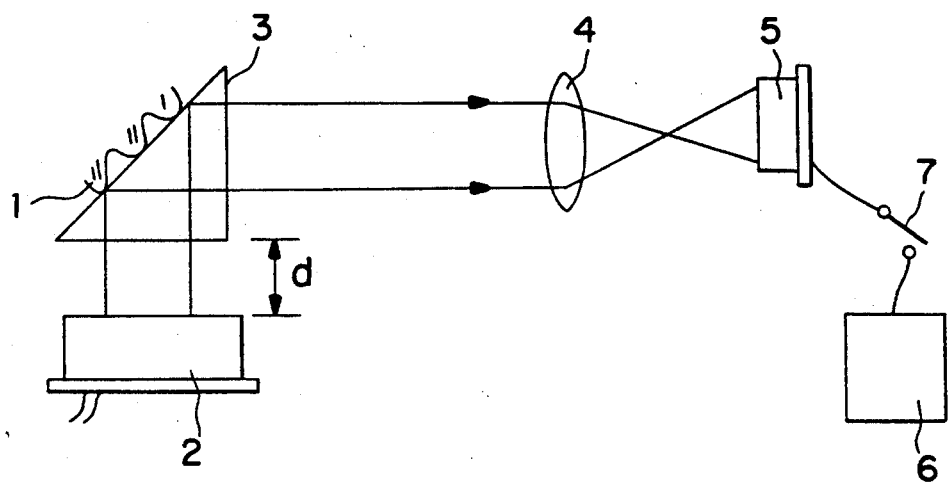
FIG. 1 shows a conventional fingerprint identification apparatus.
Figure 2:
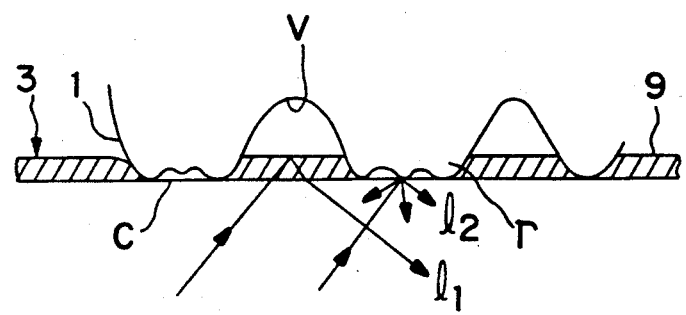
FIG. 2 shows the case where a fingerprint is placed on the rectangular prism of the conventional fingerprint identification apparatus.
Figure 3:
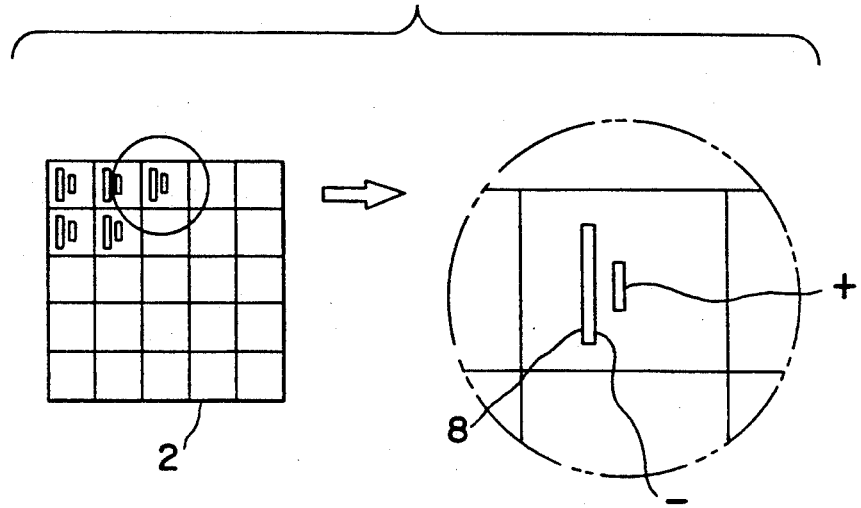
FIG. 3 is a plane view of the multiple LED of the conventional fingerprint apparatus.
Figure 4:
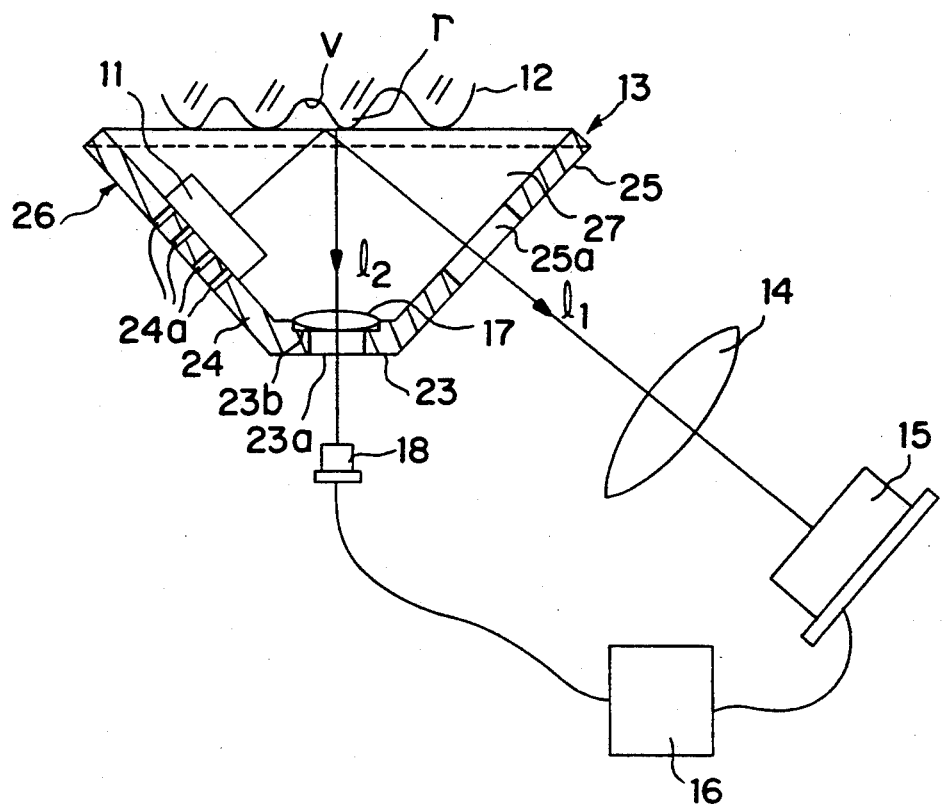
FIG. 4 shows a fingerprint identification apparatus according to an embodiment of the present invention.

A fingerprint identification apparatus according to an embodiment of the present invention includes, as shown in FIG. 4, an illuminating LED 11 used as an illumination source, a light conducting panel 13 for placing a fingerprint 12, an imaging lens 14 for forming an image from the light totally reflected from the valley areas of the fingerprint placed on the light conducting panel 13, a CCD 15 for converting the image formed by the imaging lens 14 to an electrical signal, a signal processing circuit 16 for analyzing and identifying the fingerprint image converted to the electrical signal by the CCD 15, a light concentration lens 17 for concentrating the light 12 diffused from the ridge areas of the fingerprint placed on the light conducting panel 13, and a sensing device 18 for detecting whether the fingerprint is placed on the light conducting panel 13 or not and activating the signal processing circuit 16.

Figure 6A:
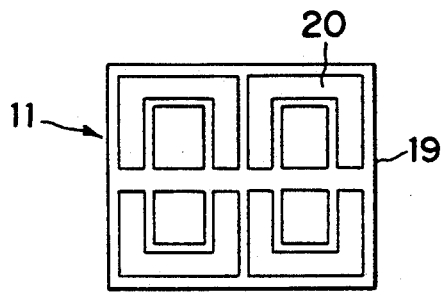
FIG. 6A is a plane view of the illuminating LED according to an embodiment of the present invention.
Figure 6B:
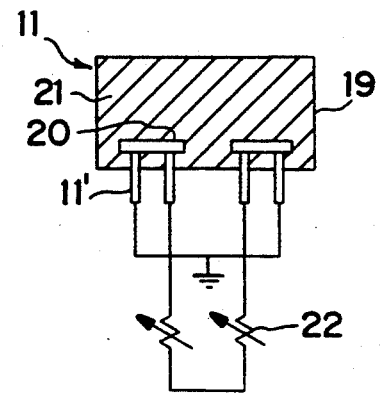
FIG. 6B is a cross-sectional view of the illuminating LED according to an embodiment of the present invention.

The illuminating LED 11 according to an embodiment of the present invention has a number of high ultra-luminance LED chips 20 (4 chips are shown in FIG. 6A), in which the light intensity is three times that of the common LEDs within a case 19, as shown in FIG. 6A and 6B. Also, the upper part of the illuminating LED 11 is coated with a diffuser compound 21 of a regular thickness (about 5 mm) to prevent the formation of a chip image on CCD 15 when the light is radiated from the high ultra-luminance chips 20. In addition, a rheostat 22 is installed on the high ultra-luminance chips 20 to control the light intensity depending upon the distance between the light conducting panel 13 and the high ultra-luminance chips 20. As a result, the fingerprint image formed on the CCD 15 is enabled to maintain a uniform brightness through a reduction of the optical path difference between the illuminating LED 11 and the CCD 15.

The light conducting panel 13 includes silicone 27 filled in a trapezoidal hexahedral housing 26 which in the illuminating LED 11 and the light concentration lens 17 are mounted, and the critical angle of silicone is $$(\theta) = \mathrm{Sin}\ (1/n)45° \quad (n = \text{refractive index})$$

In addition, there is a hole 23a on the central part of the frontal wall 23 of the trapezoidal hexahedral housing 26 for passing the light reflected from the ridge areas r of the fingerprint 12, and a fixed socket unit 23b on the opposite side of the light conducting panel 13 for mounting the light concentration lens 17 to concentrate the light diffused from the ridge areas of the fingerprint 12 being placed on the light conducting panel 13. The illuminating LED 11 is fixed onto the side wall 24 of the housing 26, and a number of fixed perforations 24a are provided for inserting of the terminal pins 11' of the illuminating LED 11.

In addition, the other side wall 25 opposite to the side wall 24 having the illumination LED 11 mounted thereon is made of glass, and has another hole 25a provided for passing the light 1 totally reflected from the valley areas v of the fingerprint 12, The and the outside of the side wall 25 is covered with an opaque coating layer, so that formation of light noise by the imaging lens 14 can be prevented and only the light corresponding to fingerprint image will pass therethrough.

Figure 5A:
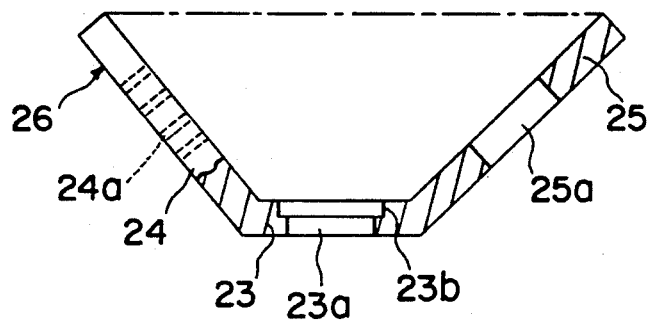
FIG. 5A is a cross-sectional view of the light conducting panel according to an embodiment of the present invention.
Figure 5B:
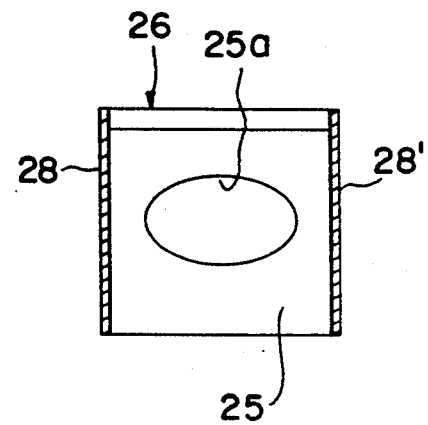
FIG. 5B is a right side view of FIG. 5A.

The light concentration lens 17 is mounted onto the fixed socket 23b of the housing 26 and the terminal pins 11' o f the illuminating LED 11 are inserted into the fixed perforations 24a on the side wall 24. As shown in FIG. 5A, silicone compound is applied to the inner part of the housing 26 after both front and rear sides of the housing 26 are covered with thin vinyl 28, 28' formed in air holes (not shown) to facilitate shaping of the molding materials. If the silicone has dried under natural conditions in a place free from pollution material such as dust, the silicone compound hardens, making it possible to form the light conducting panel 13 and the illuminating LED 11 into a single body, as shown in FIG. 4.

Further, it is desirable to use a photoelectric sensor like a photo diode as the sensing device 18 to activates the signal processing circuit 16.

The details of operation and effects of an embodiment of the present invention are as follows:

As shown in FIG. 4, when the fingerprint 12 is placed on the upper side of the light conducting panel 13, the light radiated from the illuminating LED 11 is totally reflected from valley areas V of the fingerprint 12 and passes through the hole 25a in the side glass wall 25. Thereby, the image of the fingerprint is formed on the CCD 15 by the imaging lens 14, and the image of the fingerprint 12 is then converted to an electrical signal at the CCD 15.

On the other hand, while the light is totally reflected from the valley areas V of the fingerprint 12, the light is diffused at the ridge areas r of the fingerprint 12 so that the diffused light is concentrated by the light concentration lens 17 and applied to the sensing device 18, i.e., a photo diode. Thus, the signal processing circuit 16 is activated and checks whether the fingerprint has been effected.

Therefore, the fingerprint image converted to the electrical signal by the CCD 15 is inputted to the signal processing circuit 16 and the signal processing circuit 16 identifies the fingerprint 12 placed on the light conducting panel 13.

One advantage of present invention is provided by the silicone 27 being molded within the housing 26 for preventing the noise produced during the process of classifying the ridge and valley areas of the fingerprint 12 because the light is diffused by the micro-gaps between the ridge areas r of the fingerprint 12 and the light conducting panel 13.

Another advantage of present invention is that the illuminating LED 11 is coated with a diffuser compound 21 of a regular thickness, so that formation of an image of the ultra-luminance chips 20 at the CCD 15 is prevented by diffusing the light radiated from the high ultra-luminance chips 20. Also, by installing each rheostat 22 and combining the terminal pins 11' of the high ultra-luminance chips 20 into two rows, the light intensity difference can be compensated by controlling the resistance value of the rheostat 22 depending upon the distance between the fingerprint 12 on the light conducting panel 13 and the illuminating LED 11 as shown in FIG. 6. This, in turn, enables a uniform brightness to be maintained for the fingerprint image formed on the CCD 15 and enhances the reliability of the apparatus.

Also by applying an opaque coating layer on the side glass wall 25 of the housing 26, the apparatus can exclude the light, except for light of the fingerprint image from arriving to the imaging lens 14.

An additional advantage of present invention is to facilitate the assembly of the apparatus by making the illuminating LED 11 and the light conducting panel 13 into one body.

A further advantage of present is that, when the fingerprint 12 is placed on the light conducting panel 13, the sensing device 18 detects the fingerprint and identifies the fingerprint image accurately without the need to operate a separate switch.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A fingerprint identification apparatus, comprising:
   a housing having an illumination source for illuminating a fingerprint by radiating light, said illumination source including,
   a plurality of ultra-luminance chips,
   a diffuser coating layer for diffusing light radiation from said plurality of ultra-luminance chips,
   a rheostat for maintaining a uniform brightness by controlling a resistance value to form a clear image of said fingerprint;
   a light conducting panel for placing said fingerprint thereon and being illuminated from the light by the light radiated from said illumination source, and
   a light concentration lens for concentrating the light diffused from the fingerprint;
   an imaging lens for forming a fingerprint image from said light totally reflected from said fingerprint placed on said light conducting panel;
   a CCD for converting said fingerprint image formed by said imaging lens to an electrical signal;
   a signal processor for analyzing and identifying said fingerprint image converted to said electrical signal by said CCD; and
   a sensor for detecting said light concentrated by said light concentration lens and activating said signal processor.

2. The fingerprint identification apparatus of claim 1, wherein said light conducting panel includes a silicone molding within said housing having a regular thickness.

3. The fingerprint identification apparatus of claim 1, wherein said housing further includes a hole in order to pass said light totally reflected from said fingerprint.

4. The fingerprint identification apparatus of claim 3, wherein said housing is coated with an opaque material in order to prevent the formation of image noise of said fingerprint.

5. The fingerprint identification apparatus of claim 1, wherein said sensor includes a photoelectric element activated by said light concentrated by said light concentration lens.

* * * * *